United States Patent [19]

Arena

[11] 4,380,680
[45] Apr. 19, 1983

[54] METHOD FOR HYDROGENATING AQUEOUS SOLUTIONS OF CARBOHYDRATES

[75] Inventor: Blaise J. Arena, Des Plaines, Ill.

[73] Assignee: UOP Inc., Des Plaines, Ill.

[21] Appl. No.: 380,809

[22] Filed: May 21, 1982

[51] Int. Cl.³ .................. C07C 31/26; C07C 31/24; C07C 31/18

[52] U.S. Cl. .................................................... 568/863

[58] Field of Search ........................................ 568/863

[56] References Cited

U.S. PATENT DOCUMENTS

| | | | |
|---|---|---|---|
| 2,752,399 | 6/1956 | Grimme et al. | 568/863 |
| 3,651,221 | 3/1972 | Conrad et al. | 568/863 |
| 3,963,788 | 6/1976 | Kruse et al. | 568/863 |
| 3,963,789 | 6/1976 | Kruse et al. | 568/863 |
| 4,072,628 | 2/1978 | Kruse et al. | 568/863 |

*Primary Examiner*—Joseph E. Evans
*Attorney, Agent, or Firm*—James R. Hoatson, Jr.; Eugene I. Snyder; William H. Page, II

[57] ABSTRACT

Zerovalent Group VIII metals dispersed on alpha-alumina are hydrothermally stable hydrogenation catalysts which may be used advantageously in the reduction of aqueous solutions of carbohydrates. The use of ruthenium on alpha-alumina in the hydrogenation of glucose affords sorbitol in excellent yields with quite high selectivity, and with minimal leaching of either ruthenium or alumina.

11 Claims, No Drawings

# METHOD FOR HYDROGENATING AQUEOUS SOLUTIONS OF CARBOHYDRATES

BACKGROUND OF THE INVENTION

In hydrogenating organic materials using zerovalent metal catalysts, it is more common to use the metal dispersed on an inert support than to use, for example, colloidal dispersions of the metal itself. Included among advantages accruing to supported metals are their greater surface activity, leading to increased reactivity, and their greater ease of separation, as by filtration. Colloidal metals are notoriously difficult to separate by filtration, and incomplete removal and recovery is costly and often deleterious to the product of hydrogenation.

When hydrogenations are conducted in aqueous media, the lack of hydrothermal stability of the commonly used supports places severe limitations on catalyst lifetime and recovery and also on the quality of the product due to dissolved support material. Where such hydrogenations are of hydroxylic organic compounds, the problem of hydrothermal instability of support materials is intensified. Where the organic compounds are polyhydroxylic, such as carbohydrates, the problem of hydrothermal instability is particularly exacerbated because of the relatively high concentration of hydroxyl groups from both water as solvent and the material to be hydrogenated.

The irony in hydrogenating aqueous solutions of carbohydrates is two-fold. First, the reduction products of many carbohydrates are important materials of commerce; sorbitol and mannitol are but two common reduction products. Additionally, there is no practical alternative to using water as the solvent in hydrogenating carbohydrates because carbohydrates generally are insoluble or, at best, sparingly soluble in most organic solvents. Because carbohydrates are solids, it is operationally mandatory to use a solvent in their hydrogenation.

It is an object of this invention to hydrogenate carbohydrates in aqueous media using as a catalyst a zerovalent metal on a hydrothermally stable support. An embodiment comprises a method of hydrogenating an aqueous solution of a carbohydrate where the catalyst is a Group VIII zerovalent metal dispersed on a support of alpha-alumina. In a more specific embodiment, the metal is ruthenium. In a still more specific embodiment, the carbohydrate is a hexose.

DESCRIPTION OF THE INVENTION

The invention which is the subject matter herein is a method for the hydrogenation of a carbohydrate to its polyols comprising contacting at hydrogenation conditions an aqueous solution of the carbohydrate with hydrogen and a catalyst consisting essentially of a zerovalent Group VIII metal selected from the group consisting of osmium, ruthenium, palladium, and platinum dispersed on alpha-alumina, and recovering the formed polyols. This invention results from the discovery that alpha-alumina possesses remarkable hydrothermal stability under conditions necessary for the hydrogenation of aqueous solutions of carbohydrates, especially in comparison with the more commonly used gamma-alumina. Thus, whereas substantial amounts of silica and gamma-alumina, which are two commonly employed support materials, dissolve in the aqueous medium during hydrogenation of carbohydrates, virtually no leaching of alpha-alumina occurs under comparable hydrogenation conditions.

Therefore, one advantage of this invention is that the product contains a substantially lower level of dissolved metal from the inert support described herein than that resulting from inert supports commonly employed previously in the hydrogenation of carbohydrates.

Another advantage of this invention is that the zerovalent metals commonly employed as a hydrogenation catalyst retain their activity on the alpha-alumina support of this invention.

Yet another advantage of the invention as claimed is that of the Group VIII metals palladium, osmium, and ruthenium are more resistant to leaching under hydrogenation conditions than other metals of this class, such as nickel. Because ruthenium is both resistant to leaching and particularly catalytically active it is especially advantageous in the practice of this invention.

As mentioned previously, the invention herein is concerned with a method of hydrogenating a carbohydrate to its polyols. Carbohydrates are polyhydroxyaldehydes, polyhydroxyketones, or compounds that can be hydrolyzed to them. A carbohydrate that cannot be hydrolyzed to simpler compounds is called a monosaccharide. One that can be hydrolyzed to two monosaccharide molecules is called a disaccharide, and one that can be hydrolyzed to many monosaccharide molecules is called a polysaccharide. A monosaccharide may be classified according to the number of carbon atoms it contains; a hexose is a 6-carbon monosaccharide, a pentose is a 5-carbon monosaccharide, and a tetrose is a 4-carbon monosaccharide. Monosaccharides are preferred among the carbohydrates which may be used in this invention, and among these the hexoses, pentoses and tetroses are the most important members, with the hexoses particularly preferred.

The polyol reduction products of this invention have the formula $HOCH_2(CHOH)_nCH_2OH$, where n is 2, 3, or 4 depending upon the kind of monosaccharide used or the kind of units in the di- or polysaccharide. Where n is 4, the polyol is a hexitol; where n is 3, the polyol is a pentitol; and where n is 2, the polyol is tetritol. It is to be understood that where the carbohydrate is a disaccharide or polysaccharide, substantial hydrolysis accompanies hydrogenation to ultimately afford the polyols of this invention.

The examples of carbohydrates below are cited merely for illustration, and are not intended as exhaustive of the suitable reactants which may be used in this invention. Accordingly, monosaccharides that can be employed include glucose, mannose, galactose, talose, fructose, allose, altrose, idose, gulose, xylose, lyxose, ribose, arabinose, threose and erythrose. Glucose and mannose are particularly preferred monosaccharides which afford sorbitol and mannitol, respectively, as their polyol reduction product. Fructose is another preferred monosaccharide which affords a mixture of sorbitol and mannitol as the product. Examples of disaccharides include maltose, cellobiose, sucrose and lactose. Among the more abundant polysaccharides which may be employed in this invention are starch, cellulose and their degradation products.

The catalysts of this invention consist essentially of a zerovalent Group VIII metal dispersed on alpha-alumina. Among the metals which may be used are included ruthenium, osmium, palladium and platinum, with ruthenium being preferred because of its high resistance to leaching and particularly high catalytic activity under process conditions.

The Group VIII metal is generally dispersed on alpha-alumina as the inert support by impregnating the latter with a suitable salt of the metal, calcining the salt where necessary, and by reducing it to the zerovalent metal in a hydrogen atmosphere. Calcining is performed where volatiles are to be removed from the support, or where the metal salt needs to be converted, e.g., to its oxide, to be readily reducible. In suitable cases calcination and reduction may be combined in the same step.

It is to be understood that by alpha-alumina is meant alumina whose crystallinity as measured by X-ray diffraction corresponds to that characterized in ASTM file number 10-173. Because the surface area of alpha-alumina is relatively low, metal loadings are correspondingly low. In this invention the catalyst typically contains from about 1 to about 5% metal.

The aqueous solution of the carbohydrate is contacted with hydrogen and the catalyst of this invention at hydrogenation conditions. Hydrogenation conditions include a pressure of at least about 200 psig, with pressures in excess of about 5000 psig generally not advantageous. In the usual case, a hydrogen pressure from about 700 to about 5000 psig is used, with a pressure from about 1000 to about 3000 psig preferred. The hydrogenation temperature will be greater than about 80° C., with the upper temperature limit dictated by the onset of the decomposition of either the product or reactant. For example, in the case of glucose as the reactant and sorbitol as the product, the upper temperature limit is about 160° C. In practical terms, a hydrogenation temperature from about 100° to about 150° C. is preferred with one from about 110° to about 130° C. being especially advantageous.

The amount of catalyst used will depend, inter alia, on the amount of metal on the support, hydrogenation pressure, and temperature. In the case of ruthenium, for example, sufficient catalyst is employed to give from about 0.1 to about 1 wt. % ruthenium based on the carbohydrate as monosaccharide.

The method of this invention may be practiced in either a batch or a fixed mode. In the batch mode, an aqueous solution of the carbohydrate containing from about 25 to about 60 percent carbohydrates is loaded into a reactor containing, for example, the ruthenium on a alpha-alumina catalyst of this invention in an amount sufficient to give from about 0.1 to about 1 wt. % ruthenium based on the carbohydrate. The mixture is then heated to the desired temperature, which is from about 80° to about 160° C., and usually from about 100° to about 150° C. After the desired reaction temperature is attained, hydrogen is admitted to a pressure from about 700 to about 5000 psig. The entire reaction mixture is then agitated to provide adequate contact among the hydrogen, catalyst, and carbohydrate. The hydrogenation is continued until there is no further hydrogen uptake, which generally is a time from about 0.5 to about 5 hours.

The invention described is advantageously practiced in a continuous fashion using the catalyst in a fixed bed, fluidized bed, expanded bed, and so forth. In a typical operation, feedstock containing from about 25 to about 60% of the carbohydrate(s) to be reduced is passed, through the bed of catalyst, which is platinum, palladium, osmium, or ruthenium on alpha-alumina, in a hydrogen atmosphere. Hydrogen pressure is from about 700 to about 5000 psig, and bed temperature is generally from about 100° to about 150° C. The effluent is an aqueous solution of the formed polyol(s), which may be recovered by, for example, removal of water by evaporation.

The examples which follow merely illustrate this invention and are not intended to limit it in any way.

EXAMPLE 1

The following experiment was done to demonstrate the hydrothermal stability of various materials often used as an inert support for catalytically active zerovalent metals. A mixture of 50 ml of a 50 percent aqueous solution of sorbitol and 2.5 g of support material was held in a rotating glass-lined autoclave for 24 hours in the presence of hydrogen at 135 atmospheres and at 130° C. At the end of this period, solid was removed by filtration and the filtrate was analyzed for metals. The following table summarizes the results.

| LEACHING OF INERT SUPPORTS | |
|---|---|
| Support Material | Dissolved Support Material |
| alpha-alumina | less than 1 ppm Al |
| gamma-alumina[a] | 60 ppm Al |
| gamma-alumina[b] | 129 ppm Al |
| kieselguhr[c] | 83 ppm Si |

[a]0.5 ABD, surface area 200 m$^2$/g
[b]0.3 ABD, surface area 160 m$^2$/g
[c]Solution of glucose was used instead of sorbitol.

The results clearly show the superior hydrothermal stability of alpha-alumina relative to other commonly employed supports.

EXAMPLE 2

An aqueous solution (200 ml) of 5.2% RuCl$_3$.3H$_2$O was mixed with 152 g alpha-alumina of surface area 3 m$^2$/g, after which water was evaporated. The impregnated solid was calcined for 3 hr. under flowing nitrogen at 400° C., then reduced for 4 hr. in a hydrogen stream at 400° C. The resulting catalyst contained about 3% by weight ruthenium with an average crystallite size of 158A.

EXAMPLE 3

Continuous reductions were performed in a ⅞" I.D. vertical tube reactor with a spiral preheater and with a bed of 100 cc (135 g) catalyst as prepared in Example 2. The feedstock was a 50% aqueous solution of glucose at pH about 5.5. Hydrogen was introduced at a 10:1 molar ratio relative to glucose. Effluent was analyzed by gas-liquid phase chromatography for sorbitol, mannitol, fructose, and glucose. The following table, a composite of several runs, shows the effect of process variables on conversion and product distribution.

| Continuous Reduction of Glucose with 3% Ru-alpha Alumina | | | | | | | |
|---|---|---|---|---|---|---|---|
| P[a] | T[b] | mode[c] | LHSV[d] | Conversion[e] | sorbitol | Selectivity[f] mannitol | fructose |
| 1500 | 120 | upflow | 1.0 | 60 | 96 | 3 | 1 |
| 1500 | 120 | upflow | 0.5 | 95 | 96 | 2 | 0 |
| 1500 | 120 | upflow | 0.25 | 98 | 93 | 3 | 0 |
| 700 | 120 | upflow | 1.0 | 43 | 95 | 2 | 3 |
| 700 | 120 | upflow | 0.5 | 61 | 95 | 3 | 1 |
| 700 | 120 | upflow | 0.25 | 95 | 94 | 5 | 0 |
| 700 | 120 | downflow | 1.0 | 56 | 96 | 1 | 0 |
| 700 | 120 | downflow | 0.5 | 80 | 96 | 1 | 0 |
| 700 | 120 | downflow | 0.25 | 98 | 95 | 2 | 0 |

Continuous Reduction of Glucose with 3% Ru-alpha Alumina

| $p^a$ | $T^b$ | mode$^c$ | LHSV$^d$ | Conversion$^e$ | sorbitol | Selectivity$^f$ mannitol | fructose |
|---|---|---|---|---|---|---|---|
| 1500 | 120 | upflow | 0.5 | 95 | 97 | 0 | |
| 1500 | 130 | upflow | 0.5 | 96 | 95 | 4 | |
| 1500 | 140 | upflow | 0.5 | 97 | 92 | 6 | |
| 700 | 120 | upflow | 1.0 | 43 | 95 | 1 | 3 |
| 1500 | 120 | upflow | 1.0 | 62 | 96 | 3 | 1 |
| 2000 | 120 | upflow | 1.0 | 72 | 97 | 1 | 0 |
| 700 | 120 | downflow | 1.0 | 57 | 95 | 1 | 0 |
| 1500 | 120 | downflow | 1.0 | 78 | 95 | 1 | 0 |
| 2000 | 120 | downflow | 1.0 | 85 | 96 | 1 | 0 |

$^a$Hydrogen pressure, psig.
$^b$Temperature, °C.
$^c$Feedstock passed upflow or downflow.
$^d$Liquid hourly space velocity.
$^e$Percent glucose reacted.
$^f$Selectivity is the percentage of any one product relative to total product formation.

The data show that sorbitol can be formed with a selectivity in excess of 95% at glucose conversions about 95%.

What is claimed is:

1. A method for the hydrogenation of a carbohydrate to its polyol(s) comprising contacting at hydrogenating conditions an aqueous solution of the carbohydrate with hydrogen and a catalyst consisting essentially of a zerovalent Group VIII metal selected from the group consisting of osmium, ruthenium, palladium and platinum dispersed on alpha-alumina, and recovering the formed polyol(s).

2. The method of claim 1 where the carbohydrate is a monosaccharide.

3. The method of claim 2 where the monosaccharide is selected from the group consisting of hexoses, pentoses, and tetroses.

4. The method of claim 3 where the monosaccharide is a hexose and the polyol is a hexitol.

5. The method of claim 4 where the hexose is glucose or mannose and the hexitol is sorbitol or mannitol, respectively.

6. The method of claim 4 where the hexose is fructose and the polyol is a mixture of sorbitol and mannitol.

7. The method of claim 1 where the metal is ruthenium.

8. The method of claim 1 where the hydrogenation conditions include a hydrogen pressure from about 700 to about 5000 psig and a temperature from about 80° to about 160° C.

9. The method of claim 8 where the pressure is from about 1000 to about 3000 psig.

10. The method of claim 8 where the temperature is from about 100° to about 150° C.

11. The method of claim 10 where the temperature is from about 110° to about 130° C.

* * * * *